(12) United States Patent
Yoon et al.

(10) Patent No.: US 8,649,003 B2
(45) Date of Patent: Feb. 11, 2014

(54) MICROREFRACTOMETER USING DEFOCUSING IMAGING

(75) Inventors: Sang Youl Yoon, Gwangju (KR); Sung Yang, Gwangju (KR)

(73) Assignee: Gwangju Institute of Science and Technology, Buk-Gu, Gwangju (KR)

( * ) Notice: Subject to any disclaimer, the term of this patent is extended or adjusted under 35 U.S.C. 154(b) by 0 days.

(21) Appl. No.: 13/703,805

(22) PCT Filed: Sep. 7, 2011

(86) PCT No.: PCT/KR2011/006620
§ 371 (c)(1),
(2), (4) Date: Dec. 12, 2012

(87) PCT Pub. No.: WO2012/033341
PCT Pub. Date: Mar. 15, 2012

(65) Prior Publication Data
US 2013/0208266 A1 Aug. 15, 2013

(30) Foreign Application Priority Data

Sep. 8, 2010 (KR) ........................ 10-2010-0087744

(51) Int. Cl.
*G01N 21/41* (2006.01)

(52) U.S. Cl.
CPC .................................. *G01N 21/4133* (2013.01)
USPC ........................................................ 356/128

(58) Field of Classification Search
USPC .................................................. 356/128–137
See application file for complete search history.

(56) References Cited

U.S. PATENT DOCUMENTS

| 4,353,649 | A | * | 10/1982 | Kishii | 356/33 |
| 5,309,214 | A | * | 5/1994 | Hashimoto | 356/128 |
| 5,355,211 | A | * | 10/1994 | Thompson et al. | 356/135 |
| 2004/0145731 | A1 | * | 7/2004 | Nakajima et al. | 356/135 |

* cited by examiner

*Primary Examiner* — Hoa Pham
(74) *Attorney, Agent, or Firm* — Nath, Goldberg & Meyer; Jerald L. Meyer; Scott Langford

(57) ABSTRACT

The present invention relates to a microrefractometer using defocusing imaging. The refractometer includes: a target in which a target micrometer and a reference fluid, an index of refraction of which is known, are positioned; an objective lens receiving light that has been emitted from a light source and passed through the target; an aperture including a plurality of pin holes which divide an optical path of the light having passed through the objective lens; and a camera photographing defocused images formed on an image plane of the refractometer by the light having passed through the aperture.

19 Claims, 8 Drawing Sheets

(a)

(b)

US 8,649,003 B2

MICROREFRACTOMETER USING DEFOCUSING IMAGING

This is a National Phase Application filed under 35 U.S.C. §371 as a national stage of International Application No. PCT/KR2011/006620, filed on Sep. 7, 2011, claiming the benefit from Korean Patent Application No. 10-2010-0087744 filed on Sep. 8, 2010, the content of each of which is hereby incorporated by reference in its entirety.

TECHNICAL FIELD

The present invention relates to a microrefractometer using defocusing imaging, and more particularly, to a technology of forming multiple defocused images on an image plane using an aperture for separating optical paths of light to measure an index of refraction of a microfluid based on a diameter of a circumscribed circle connecting the multiple defocused images to each other.

BACKGROUND ART

In general, an index of refraction is a natural property of a material measured according to an optical method. In particular, an index of refraction is mainly used to induce properties of a fluid in the fields of biochemistry and biomedicine since it is influenced by the content of a solute in a solvent.

Conventionally, refractometers for measuring an index of refraction of a microfluid have been studied in various ways. However, there is a limit in accurately measuring an index of refraction of a small amount of a target fluid.

For example, although there have been attempts to measure an index of refraction of a microfluid using an Abbe prism, a Fabry-Perot resonator, a Bragg reflector resonator, and a microchannel edge image, these apparatuses require a complex manufacturing process and high costs. Further, these apparatuses cause uncertainty in measurement of the index of refraction of the microfluid according to user skill, and a separate calibration procedure is necessarily performed to measure the index of refraction using a refractometer in most cases.

Therefore, there is a need for a microfluid measuring refractometer capable of easily and accurately measuring an index of refraction using a self-calibration type simple system has arisen.

DISCLOSURE

Technical Problem

The present invention has been conceived to solve such problems in the art, and a first aspect of the present invention is to provide a microrefractometer that can measure an index of refraction of a microfluid based on a diameter of a circumscribed circle connecting defocused images using defocusing imaging.

A second aspect of the present invention is to provide a microrefractometer that can simultaneously form defocused images of a target microfluid and a reference fluid, an index of refraction of which is known, to measure an index of refraction of the target microfluid in order to achieve self-calibration upon measurement of the index of refraction of the microfluid.

In relation to the first aspect of the present invention, another aspect of the present invention is to provide an aperture including a plurality of pin holes to form defocused multiple images by diversifying an optical path of light.

The technical aspects of the present invention are not limited to these aspect and other aspects of the present invention will become apparent to those skilled in the art from the following description.

Technical Solution

In accordance with one aspect of the present invention, a refractometer for measuring an index of refraction of a microfluid including: a target in which a target microfluid is positioned; an objective lens receiving light that has been emitted from a light source and passed through the target; and an aperture including a plurality of pin holes that divide an optical path of the light having passed through the objective lens to form defocused images on an image plane of the refractometer.

The target may include a measurement region in which the target microfluid is positioned; and a calibration region in which a reference fluid, an index of refraction of which is known, is positioned to measure an index of refraction of the target microfluid.

At least two reference fluids may be positioned in the calibration region and have different indexes of refraction.

The measurement region may include a sample channel in which the microfluid is positioned, and the calibration region may include a plurality of reference channels such that the reference fluids do not interfere with each other.

Each of the sample channel and the reference channels may include a plurality of opaque patterns arranged at constant intervals in a row, and each of the opaque patterns may be provided at a central portion thereof with a transparent spot through which light passes.

The opaque patterns may be formed by sputtering chromium.

The aperture may include at least two pin holes arranged at constant intervals. Most preferably, the aperture includes three pin holes.

Images corresponding to the target microfluid and the reference fluid may be simultaneously formed on the image plane.

An index of refraction of the target microfluid may be determined depending on a diameter of a circumscribed circle connecting the defocused images.

In accordance with another aspect of the present invention, a refractometer for measuring an index of refraction of a microfluid includes: a target in which a target microfluid and a reference fluid, an index of refraction of which is known, are positioned; an objective lens receiving light that has been emitted from a light source and passed through the target; an aperture including a plurality of pin holes that divide an optical path of the light having passed through the objective lens; and a camera photographing defocused images formed on an image plane of the refractometer by the light having passed through the aperture.

The refractometer may further include: an optical filter disposed between the aperture and the camera or between the target and the light source to filter a wavelength of the light emitted from the light source.

The target may include a measurement region in which the target microfluid is positioned; and a calibration region in which the reference fluid is positioned to measure an index of refraction of the target microfluid.

At least two reference fluids may be positioned in the calibration region and may have different indexes of refraction.

The measurement region may include a sample channel in which the microfluid is positioned, and the calibration region may include a plurality of reference channels such that the reference fluids do not interfere with each other.

Each of the sample channel and the reference channels may include a plurality of opaque patterns arranged at constant intervals in a row, and each of the opaque patterns may be provided at a central portion thereof with a transparent spot through which light passes.

The aperture may include three pin holes, and the pin holes may be arranged at constant intervals. Alternatively, the aperture may include at least two pin holes and intervals between the pin holes may be arbitrarily determined.

Images corresponding to the target microfluid and the reference fluid may be simultaneously formed on the image plane.

Advantageous Effects

According to the present invention, the microrefractometer may easily measure an index of refraction of a micro-material based on the diameter of a circumscribed circle connecting plural defocused images.

In addition, according to the present invention, the microrefractometer may form defocused images of a target microfluid and defocused images of a reference fluid at the same time on an image plane thereof to achieve self-calibration upon measurement of an index of refraction of a microfluid.

BEST MODE

Figure 1:
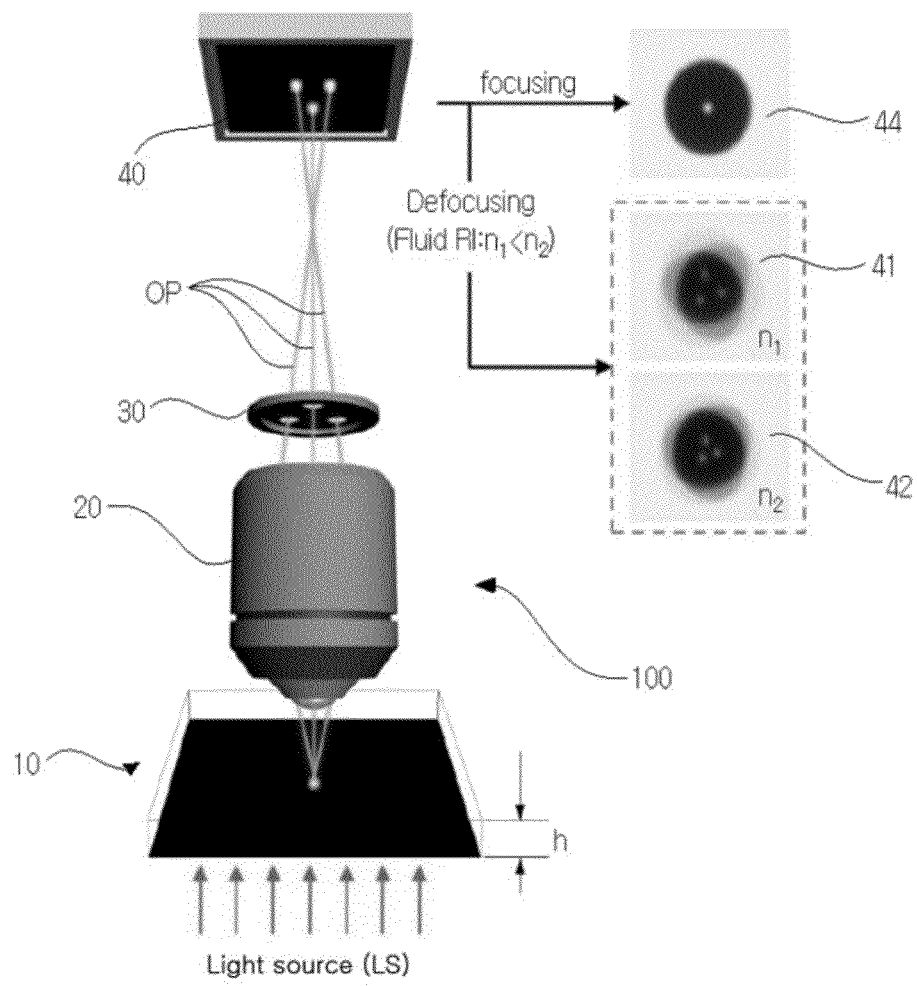
FIG. 1 is a schematic diagram of a microrefractometer according to one embodiment of the present invention.

Hereinafter, exemplary embodiments of the present invention will be described in detail with reference to the accompanying drawings. It will be understood that when an element is referred to as being connected to or being on another element, it can be directly on the other element, or intervening elements may also be present. Further, it should be understood that like elements will be denoted by like reference numerals throughout the accompanying drawings. Further, it should be understood that configurations and operations of the present invention illustrated in the drawings and described therewith are provided as at least one exemplary embodiment and the scope and sprit of the present invention are not limited thereto.

FIG. 1 is a schematic diagram of a microrefractometer according to one embodiment of the present invention.

Referring to FIG. 1, a microrefractometer 100 according to the present embodiment includes a target 10, an objective lens 20, and an aperture 30.

The target 10 is a device in which a target microfluid is positioned, and the objective lens 20 receives light which has emitted from a light source LS and passed through the target 10. The aperture 30 is located at a rear side of the objective lens 20 and divides the light having passed through the objective lens 20 to project images created by divided light components OP to an image plane 40. The objective lens 20 may be any one known in the art, and a detailed description thereof will be omitted herein.

Although the aperture 30 may include a plurality of pin holes, the microrefractometer 100 will be illustrated as including three pin holes in this embodiment.

In the microrefractometer 100, the aperture 30 includes three pin holes and the microfluid is positioned in the target 10. Thus, when light emitted from the light source passes through the target 10 and is finally focused on the image plane 40 by an index of refraction of the microfluid, defocused images 41, 42 are generated. This phenomenon will be described in detail with reference to FIG. 2.

Figure 2:
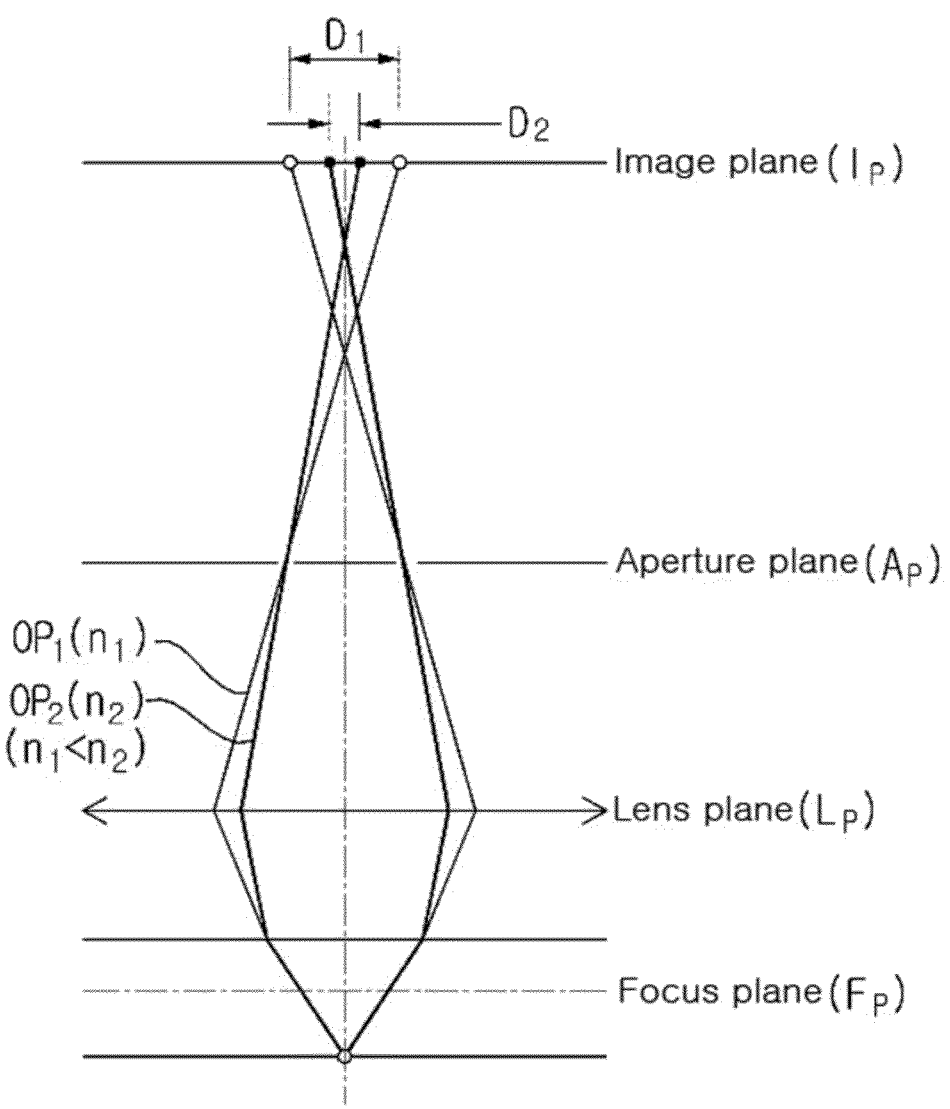
FIG. 2 shows a relationship between an index of refraction of a microfluid and defocused images in the microrefractometer according to the embodiment of the present invention.

FIG. 2 shows a relationship between an index of refraction of a microfluid and defocused images in the microrefractometer according to the embodiment of the present invention.

Referring to FIG. 2, once light have passed through a focus plane Fp on which a microfluid is present, the light is refracted at an interface of the microfluid, air, or a border surface such as a glass surface forming the surface of the target. Here, when factors other than the index of refraction of the microfluid, that is, air or the border surface such as the glass surface are fixed, refraction of the light is influenced only by the index of refraction of the microfluid. In this way, the light emitted from the light source passes through a lens plane Lp and an aperture plane Ap, and is finally focused on an image plane IP through different degrees of refraction (optical paths) by indexes of refraction of microfluids.

In this way, since different optical paths are formed by the microfluids having different indexes of refraction, the images formed on the image plane IP have different degrees of defocusing (that is, degree of separation between spot images). In FIG. 2, an index of refraction $n_1$ is smaller than an index of refraction $n_2$, and a degree of defocusing $D_1$ of an image formed on the image plane Ip is larger than a degree f defocusing $D_2$ of an image formed on the image plane Ip. That is, a microfluid having a larger index of refraction shows a smaller degree of defocusing.

As shown in FIG. 2, when all parameters are fixed except for the index of refraction of the microfluid, the degree of separation between respective spot images in the defocused images depend only on the index of refraction of the microfluid. Thus, the index of refraction RI of the microfluid may be measured using the separation degree of the defocused images.

However, in this case, measurement of the index of refraction requires a calibration process due to complexity of the optical paths and difficulty in approaching optical characteristics of a micro optical apparatus.

Thus, according to the present invention, in measuring an index of refraction of a target microfluid, an image of a reference fluid, an index of refraction of which is known, is formed together with an image of the target microfluid to achieve self-calibration of the microrefractometer. In detail, this is realized by improving the structure of the target of the microrefractometer. Next, the structure of the target used in the present invention will be described in detail.

Figure 3:
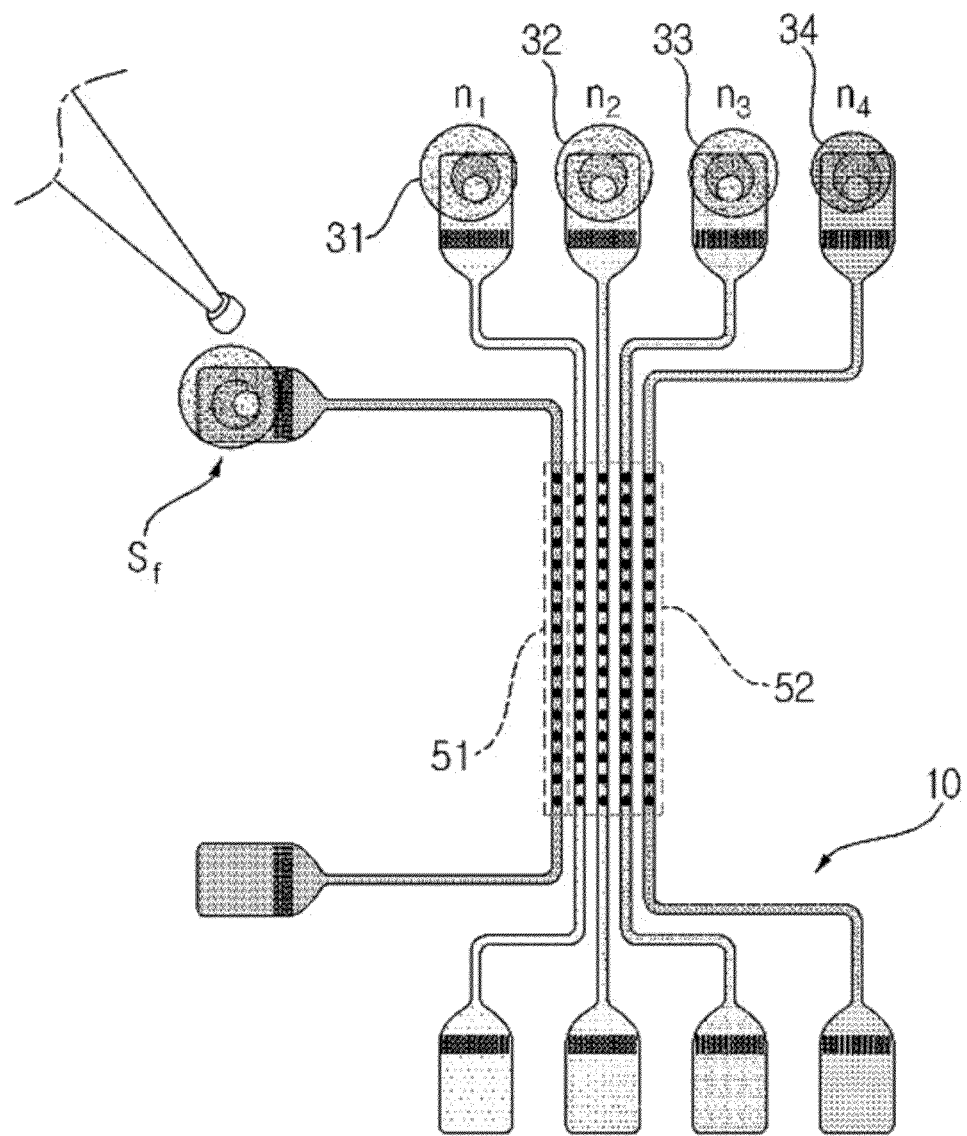
FIG. 3 shows a diagram of a target of the microrefractometer according to the embodiment of the present invention.
Figure 4:
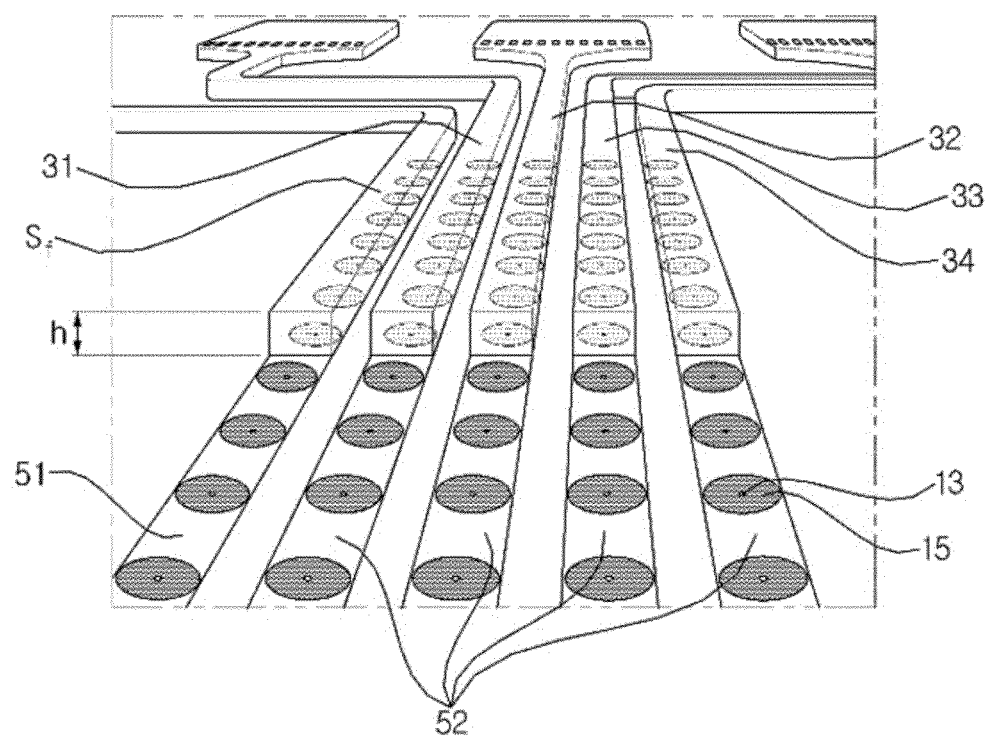
FIG. 4 is a detailed diagram of the structure of the target of FIG. 3.
Figure 5:
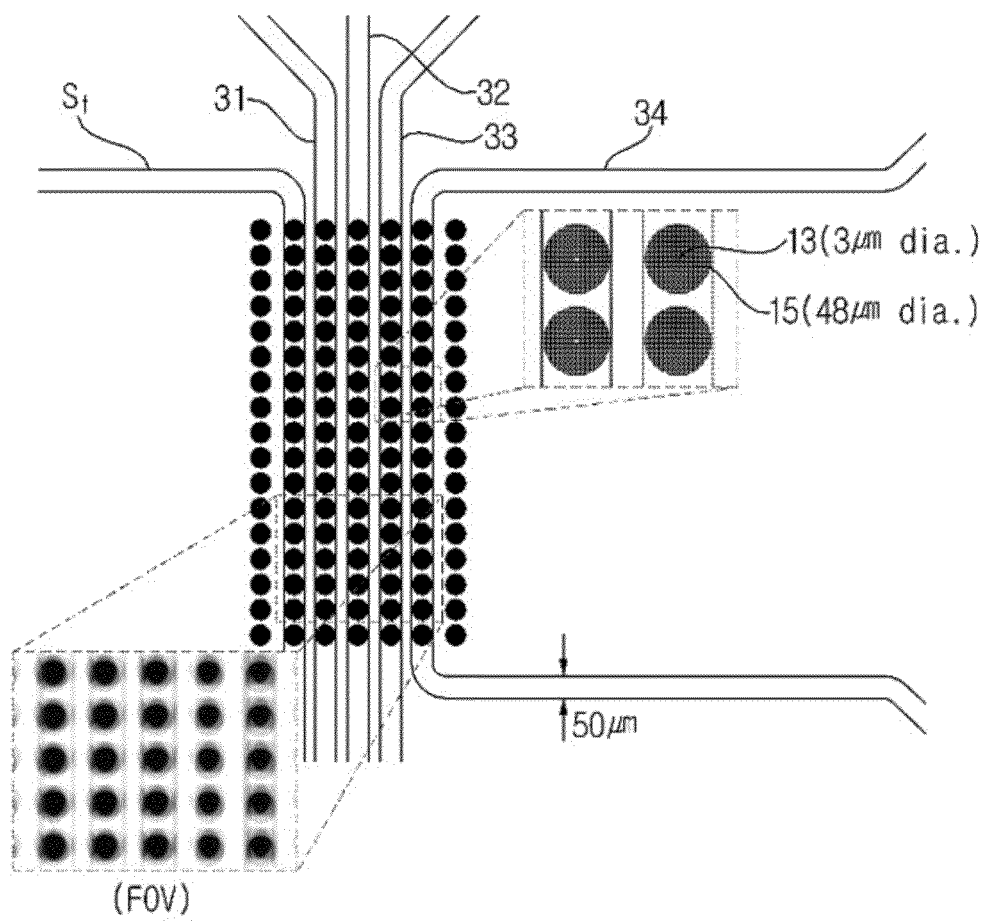
FIG. 5 is a diagram showing an image formed on an image plane in the microrefractometer according to the embodiment of the present invention.

FIG. 3 shows a diagram of a target of the microrefractometer according to the embodiment of the present invention, FIG. 4 is a detailed diagram of the structure of the target of FIG. 3, and FIG. 5 is a diagram showing an image formed on an image plane in the microrefractometer according to the embodiment of the present invention.

Referring to FIG. 3, a target microfluid Sf and reference fluids 31, 32, 33, 34 are positioned in the target 10. Further, a portion of the target 10 in which the microfluid Sf is positioned may be referred to as a measurement region, and portions of the target 10 in which the reference fluids 31, 32, 33, 34 are positioned may be referred to as calibration regions.

As shown in FIG. 4, the target 10 may include, for example, five channels. Specifically, one channel (sample channel) is provided in the measurement region 51 in which the microfluid Sf is positioned, and four channels (reference channels) are provided in calibration regions 52 in which the reference fluids 31, 32, 33, 34 are positioned. The reference fluids having different indexes of refraction are positioned in different reference channels. As can be seen from the meaning of the term "reference fluid", the indexes of refraction are known.

As described above, the target 10 includes the sample channel and the reference channels, and each of the channels include an opaque pattern 15 formed on the bottom thereof. The opaque pattern 15 is opaque except for a central portion thereof, at which a transparent spot 13 is formed, such that light emitted from the light source can pass through the transparent spot 13. The opaque pattern is generally formed by sputtering chromium, without being limited thereto. That is, any material known in the art may be used to form the opaque pattern. Alternatively, a transparent pattern may be formed on the bottom of the channel and may be transparent except for a central portion thereof at which an opaque spot is formed.

Further, all of the channels formed in the target 10 have the same height h. Thus, the parameters regarding the channel heights can be neglected.

In order to achieve self-calibration in measurement of the index of refraction through the microrefractometer, defocused images regarding the measurement region 51 and the calibration regions 52 are formed on the same image plane. (see FOV (field of view) of FIG. 5). Since all of the target microfluid Sf and the reference fluids 31, 32, 33, 34 are present on the same plane, another parameter, that is, a distance between the target 10 and the objective lens can also be neglected.

Next, an overall structure of the microrefractometer according to the embodiment of the present invention will be described.

Figure 6:
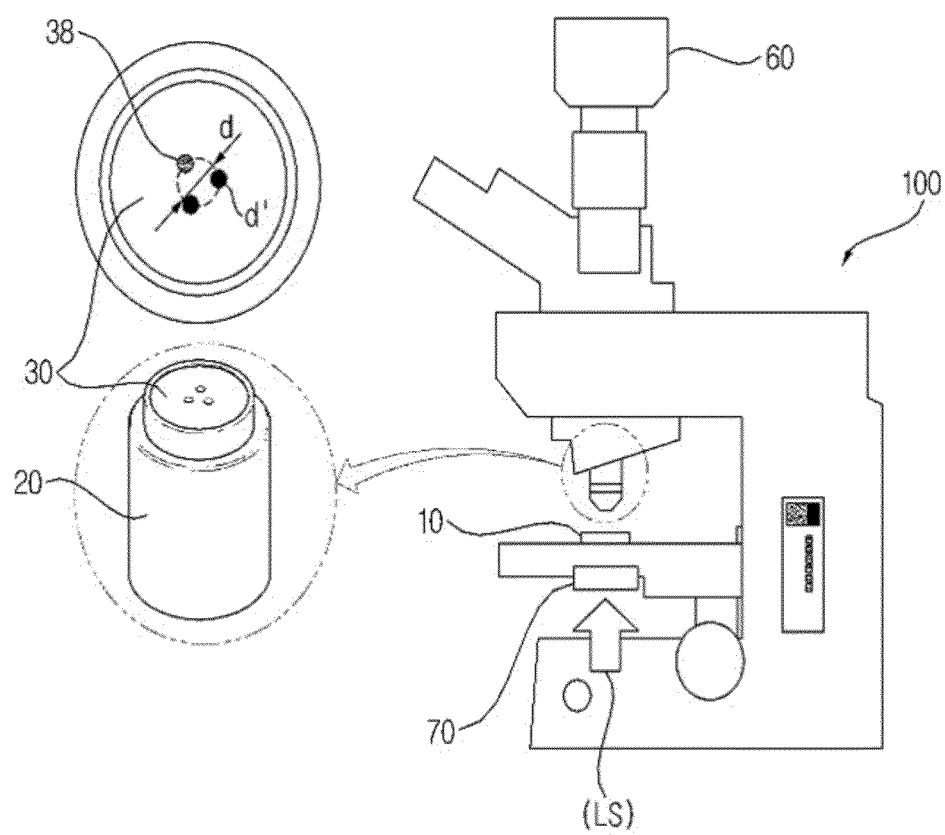
FIG. 6 is a diagram of the overall structure of the microrefractometer according to the embodiment of the present invention.

FIG. 6 is a diagram of the overall structure of the microrefractometer according to the embodiment of the present invention.

Referring to FIG. 6, the microrefractometer 100 includes a target 10, an objective lens 20, an aperture 30, a camera 60, and an optical filter 70. Here, the target 10, the objective lens 20, and the optical filter 70 are the same as those described above, and the camera 60 and the aperture 30 will be described.

The camera 60 is adapted to photograph images formed on an image plane 40 (see FIG. 1) by light having passed through the aperture 30, and may generally employ a CCD camera. The aperture 30 has three pin holes 38, and d denotes a diameter of an imaginary circumscribed circle connecting the pin holes, and d' denotes diameters of the pin holes. The diameter d may range from 1.0 mm to 5.0 mm.

Next, experiment results obtained by measuring an index of refraction of a microfluid using the microrefractometer according to the embodiment of the invention will be described.

Figure 7:
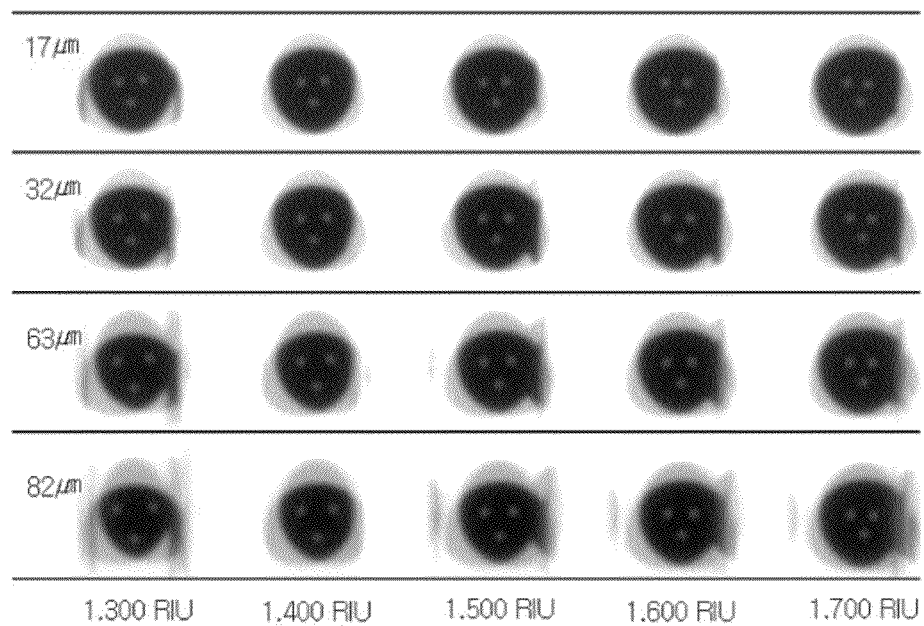
FIG. 7 is a diagram of defocused images photographed by the microrefractometer according to the embodiment of the present invention.

FIG. 7 is a diagram of defocused images photographed by the microrefractometer according to the embodiment of the present invention.

As shown in FIG. 7, the separation degree of defocused images is larger in the case of a microfluid having a low index of refraction than in the case of a microfluid having a high index of refraction. In the case of microfluids having the same refractive index, the separation degree of defocused images increases with increasing channel height f of the target. Here, the term "separation degree of defocused images" refers to an interval between image spots, and a high separation degree means that the interval between the spot images is large and sensitivity of the images is high.

Figure 8:
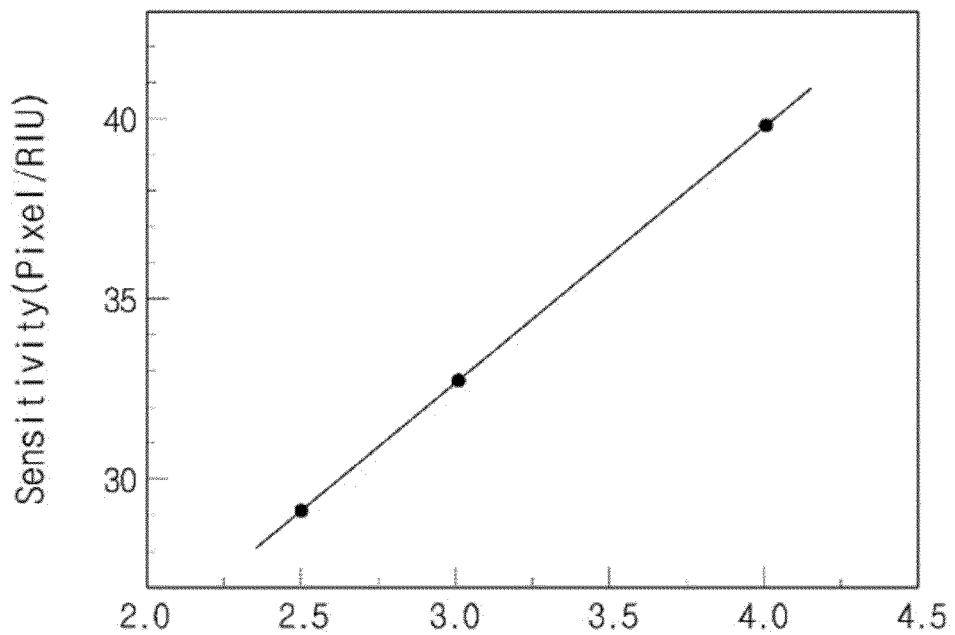
FIG. 8 is a graph depicting simulation results of measuring image sensitivities according to distances between pin holes of an aperture of the microrefractometer according to the present invention.

FIG. 8 is a graph depicting simulation results of measuring image sensitivities according to a diameter (d) of an imaginary circumscribed circle connecting pin holes of an aperture of the microrefractometer according to the embodiment of the present invention.

In FIG. 8, when channels of the target have a constant height (h) of 63 μm, the separation degree of defocused images increases with increasing interval between pin holes formed in the aperture. That is, the sensitivities are 29.16 pixels/RIU, 32.87 pixels/RIU, and 39.95 pixels/RIU, when the diameters d of the imaginary circumscribed circles connecting the pin holes of the aperture are 2.3 mm, 3.0 mm, and 4.0 mm, respectively. Thus, in accurate measurement of the index of refraction, it is more advantageous to increase the diameter (d) of the imaginary circumscribed circle connecting the pin holes of the aperture.

Figure 9:
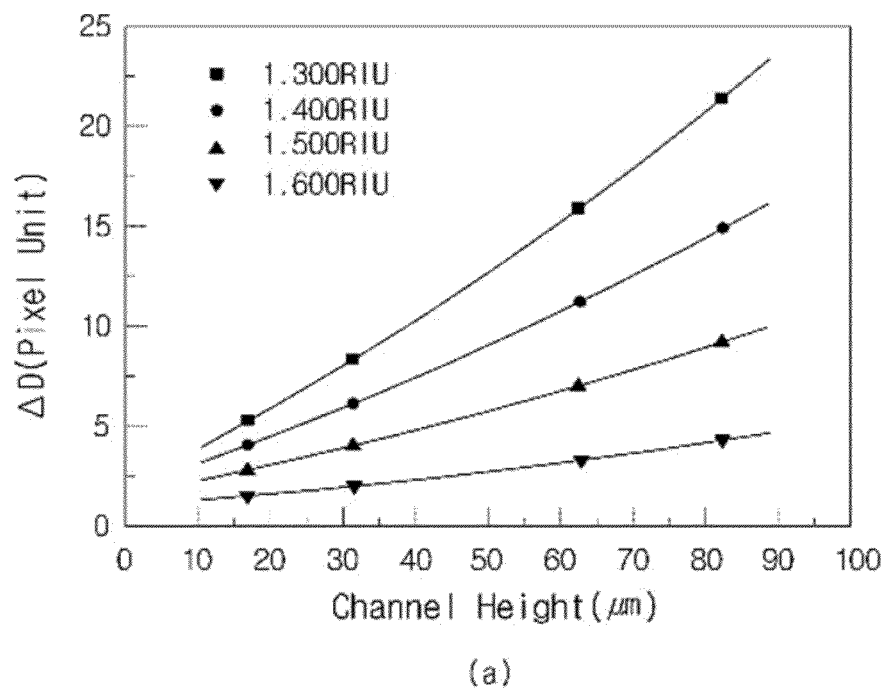
FIG. 9a is a graph depicting simulation results of measuring a separation degree of defocused images according to channel heights in a target of the microrefractometer according to the present invention.
FIG. 9b is a graph depicting simulation results of measuring a separation degree of defocused images according to indexes of refraction of microfluids in the target of the microrefractometer according to the present invention.
Figure 9:
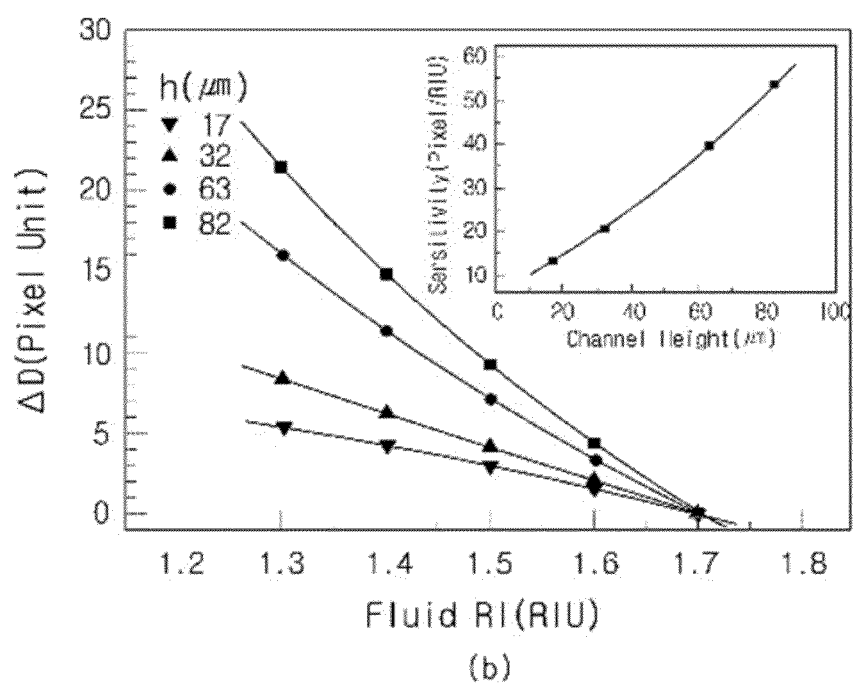

FIG. 9a is a graph depicting simulation results of measuring a separation degree of defocused images according to channel heights in a target of a microrefractometer according to the present invention.

As shown in FIG. 9a, the separation degree of defocused images substantially linearly increases with increasing channel height h of the target. Here, $\Delta D$ of the y-axis of the graph represents a difference between a diameter (D) of a circumscribed circle imaginarily connecting spot images of defocused images of a target microfluid and a diameter (DRI=1.700) of an imaginary circumscribed circle connecting spot images of defocused images of reference fluids having an index of refraction (RI) of 1.700. In the graph of FIG. 9A, $\Delta D/\Delta h$ were measured to be 0.25 pixels/μm, 0.17 pixels/μm, 0.10 pixels/μm, and 0.04 pixels/μm for the microfluids having indexes of refraction of 1.3 RIU, 1.4 RIU, 1.5 RIU, and 1.6 RIU, respectively.

FIG. 9b is a graph depicting simulation results of measuring a separation degree of defocused images according to indexes of refraction of microfluids in the target of the microrefractometer according to the present invention.

As shown in FIG. 9b, a relationship $\Delta D$ according to the indexes of refraction of the microfluids is shown. As depicted in the graph, in the case of a microfluid having a small index of refraction (RI), the separation degree (ΔD) of defocused images is low and increases with increasing channel height h of the target. Further, as can be seen from the graph in a small box of FIG. 9b, since the separation degrees (sensitivities) were measured to be 13.21 pixels/RIU, 20.61 pixels/RIU, 39.95 pixels/RIU, and 53.66 pixels/RIU when channel heights h were 17 μm, 32 μm, 63 μm, and 82 μm, respectively, it can be seen that separation degree of the images increases with increasing channel height.

Next, a result table obtained by measuring an index of refraction of a target microfluid using the microrefractometer of the present invention will be described.

TABLE 1

| Reference fluid RI for calibration | Sample RI | Measured RI mean | Standard deviation |
|---|---|---|---|
| 1.3, 1.5, 1.6, 1.7 | 1.400 | 1.4002 | ±0.0013 |
| 1.3, 1.4, 1.6, 1.7 | 1.500 | 1.4998 | ±0.0009 |
| 1.3, 1.4, 1.5, 1.7 | 1.600 | 1.6002 | ±0.0010 |

As in Table 1, when performance of the microrefractometer according to the embodiment of the present invention was examined using sample microfluids (Sample RI), indexes of refraction of which are known, mean indexes of refraction were 1.4002 for a sample having an index of refraction of 1.400, 1.4998 for a sample having an index of refraction of 1.500, and 1.6002 for a sample having an index of refraction of 1.600.

As can be seen from this result, there was only a difference of approximately 0.0002 RIU from the sample RI, and the standard deviation was approximately ±0.001 RIU.

Although some embodiments have been disclosed herein, it should be understood that these embodiments are given by way of illustration only, and that various modifications, variations, and alterations can be made without departing from the spirit and scope of the present invention. Accordingly, the scope of the present invention should be limited only by the accompanying claims and equivalents thereof.

The invention claimed is:

1. A refractometer for measuring an index of refraction of a microfluid, comprising:
   a target in which a target micrometer is positioned;
   an objective lens receiving light that has been emitted from a light source and passed through the target; and
   an aperture including a plurality of pin holes that divide an optical path of the light having passed through the objective lens to form defocused images on an image plane of the refractometer.

2. The refractometer according to claim 1, wherein the target comprises:
   a measurement region in which the target microfluid is positioned; and
   a calibration region in which a reference fluid, an index of refraction of which is known, is positioned to measure an index of refraction of the target microfluid.

3. The refractometer according to claim 2, wherein at least two reference fluids are positioned in the calibration region and have different indexes of refraction.

4. The refractometer according to claim 3, wherein the measurement region has a sample channel in which the microfluid is positioned, and the calibration region has a plurality of reference channels such that the reference fluids do not interfere with each other.

5. The refractometer according to claim 4, wherein each of the sample channel and the reference channels comprises a plurality of opaque patterns arranged at constant intervals in a row, and each of the opaque patterns is provided at a central portion thereof with a transparent spot through which light passes.

6. The refractometer according to claim 5, wherein the opaque patterns are formed by metal sputtering.

7. The refractometer according to claim 4, wherein each of the sample channel and the reference channels comprises a plurality of transparent patterns arranged at constant intervals in a row, and each of the transparent patterns is provided at a central portion thereof with an opaque spot through which light passes.

8. The refractometer according to claim 2, wherein images corresponding to the target microfluid and the reference fluid are simultaneously formed on the image plane.

9. The refractometer according to claim 8, wherein the index of refraction of the target microfluid is determined depending on a diameter of a circumscribed circle connecting the defocused images.

10. The refractometer according to claim 1, wherein the pin holes are arranged at constant intervals.

11. A refractometer for measuring an index of refraction of a microfluid, comprising:
   a target in which a target microfluid and a reference fluid, an index of refraction of which is known, are positioned;
   an objective lens receiving light that has been emitted from a light source and passed through the target;
   an aperture including a plurality of pin holes that divide an optical path of the light having passed through the objective lens; and
   a camera photographing defocused images formed on an image plane of the refractometer by the light having passed through the aperture.

12. The refractometer according to claim 11, further comprising:
   an optical filter disposed between the aperture and the camera or between the target and the light source to filter a wavelength of the light emitted from the light source.

13. The refractometer according to claim 11, wherein the target comprises:
   a measurement region in which the target microfluid is positioned; and
   a calibration region in which the reference fluid is positioned to measure an index of refraction of the target microfluid.

14. The refractometer according to claim 13, wherein at least two reference fluids are positioned in the calibration region and have different indexes of refraction.

15. The refractometer according to claim 14, wherein the measurement region comprises a sample channel in which the microfluid is positioned, and the calibration region comprises a plurality of reference channels such that the reference fluids do not interfere with each other.

16. The refractometer according to claim 15, wherein each of the sample channel and the reference channels comprises a plurality of opaque patterns arranged at constant intervals in a row, and each of the opaque patterns is provided at a central portion thereof with a transparent spot through which light passes.

17. The refractometer according to claim 11, wherein the pin holes are arranged at constant intervals.

18. The refractometer according to claim 11, wherein images corresponding to the target microfluid and the reference fluid are simultaneously formed on the image plane.

19. The refractometer according to claim 18, wherein an index of refraction of the target microfluid is determined depending on a diameter of a circumscribed circle connecting the defocused images.

* * * * *